US012551634B2

(12) United States Patent
Kaye et al.

(10) Patent No.: US 12,551,634 B2
(45) Date of Patent: Feb. 17, 2026

(54) SUBSTANCE DELIVERY DEVICE AND METHODS

(71) Applicants: Perry S Kaye, Cooper City, FL (US); Perry Scott Kaye, Cooper City, FL (US)

(72) Inventors: Perry S Kaye, Cooper City, FL (US); Perry Scott Kaye, Cooper City, FL (US)

( * ) Notice: Subject to any disclaimer, the term of this patent is extended or adjusted under 35 U.S.C. 154(b) by 773 days.

(21) Appl. No.: 17/731,256

(22) Filed: Apr. 27, 2022

(65) Prior Publication Data

US 2022/0339372 A1 Oct. 27, 2022

Related U.S. Application Data

(60) Provisional application No. 63/180,654, filed on Apr. 27, 2021.

(51) Int. Cl.
*A61M 11/04* (2006.01)

(52) U.S. Cl.
CPC ..... *A61M 11/041* (2013.01); *A61M 2205/103* (2013.01); *A61M 2205/18* (2013.01); *A61M 2205/502* (2013.01)

(58) Field of Classification Search
CPC .......... A61M 15/0003; A61M 15/0021; A61M 15/0066; A61M 15/0015; A61M 15/06; A61M 2205/14; A61M 2205/6018; A61M 2205/8206; A61M 2230/40; A61M 11/04; G16H 20/13; A24F 40/30; A24F 40/42; A24F 40/60; A24F 40/10; A24F 40/48; A24F 7/00; A61K 31/05
See application file for complete search history.

(56) References Cited

U.S. PATENT DOCUMENTS

| | | | | |
|---|---|---|---|---|
| 9,642,397 | B2 * | 5/2017 | Dai | H05B 1/0297 |
| 2016/0089508 | A1 * | 3/2016 | Smith | A61M 15/0085 128/202.21 |
| 2018/0177231 | A1 * | 6/2018 | Woodbine | H04L 67/12 |
| 2019/0167922 | A1 * | 6/2019 | Cole | A24F 40/48 |

FOREIGN PATENT DOCUMENTS

WO WO-2020165777 A1 * 8/2020

* cited by examiner

*Primary Examiner* — Kendra D Carter
*Assistant Examiner* — Maap Ellabib
(74) *Attorney, Agent, or Firm* — Diana Mederos; Mederos Legal, PLLC

(57) ABSTRACT

A substance delivery device and methods to promote treatment regimen compliance. A beneficial substance and an addictive substance are administered from a device delivering the substances by a user inhaling vaporized or atomized beneficial substances and addictive substances.

5 Claims, 5 Drawing Sheets

SUBSTANCE DELIVERY DEVICE AND METHODS

CROSS REFERENCE TO RELATED APPLICATION

This application claims priority to U.S. provisional application No. 63/180,654 having a filing date of Apr. 27, 2021, titled Substance Delivery Device and Methods, the entire contents of which is incorporated by reference.

FIELD OF THE DISCLOSURE

The present disclosure relates to devices and systems for delivering a substance to a user and methods of use thereof. More specifically, the devices and methods pertain to a system to encourage behavioral traits, routines, and treatment compliance by pairing an addictive or desirable substance with a therapeutic substance in a vaporization or atomization delivery device.

BACKGROUND OF THE DISCLOSURE

Users often use chemicals, like medical drugs, medicinal drugs, nutritional supplements, or combinations thereof, to achieve positive and beneficial outcomes. Medical treatments, medicinal treatments, nutritional regimens, and combinations thereof are designed to increase the chemical's effectiveness and confer a positive benefit on the user. While chemicals, including drugs like, but not limited to insulin, antiviral, antibacterial, antidepressants, hormones, antipsychotics, cancer treatments, and nutritional supplements like but not limited to vitamins, minerals, and extracts often perform specific tasks it is a well-known fact that they can only work if used properly and in specific manner. The chemicals cannot work if they are not taken. They can sometimes do harm if are taken in too large a quantity or with other chemicals.

To determine if a patient is responding to the treatment, it is common for testing is often also performed to determine if the chemical is working as expected or not.

For the chemicals to be effective they must often be taken over set periods of time, at set intervals and in specific dosages. Failure to comply with dose, timing, and/or intervals, in a coordinated manner can cause the chemicals to be too weak or too strong and this can cause the user to not achieve the intended benefit or worse to injure themselves. Too little of a compound can often cause the compound to be ineffective. And too much of the compound can sometimes be deadly.

Mixing chemicals can either be nonreactive, can negate the effects of one or more of the chemicals, or can modify the effects of one or more of the chemicals in either a positive, negative, or random manner. Mixing chemicals can be intentional to elicit a desired outcome or accidental which can lead to negative results including death and/or injury.

A trained medical professional will often do a drug utilization review (DRU) to ensure a person's drug regimen has the highest chance to ensure the person the best possible clinical outcome and also to avoid interactions.

A DRU of a person's regimen should take into account the best way to administer each chemical and also how the chemicals the patient will take may interact when taken together. For example, it is common for some medications to require they be taken on a full stomach while others must be taken on an empty stomach. Many types of interactions must be avoided including for example drug to drug interactions which occur when the combination of the chemicals produces an unwanted result, injury, or alters the function of the chemical. Another type of interaction is the drug to disease; where a patient's disease may be made worse by a particular drug or the drug may be too strong for an infant or child. And another is a drug to patient; for example, where a drug may harm a pregnant individual or their unborn baby. Different patient's allergies, gender, pregnancy, age (pediatric or geriatric or etc.), condition, or genetics can alter the chemical's effect On the person and must be considered. A DRU works to make sure the chemicals the person is taking have the least, preferably none, interactions, and have the best chance of success for the person.

Non-adherence is a term common in the medical community and it describes the problem of persons not maintaining adherence to their treatment regimen. For treatment to be effective a person must follow the planned regimen. The patient's condition is monitored, and the treatment regimen is updated to ensure it is effective for the patient. Without adherence to the regimen, it is difficult to know if the treatment is working because the treatment is not being applied correctly.

Testing how a treatment regimen is working for a patient is dependent on the treatment regimen being followed. For example, one cannot know if a person's health is improving due to taking a particular drug if you are not able to determine if, in fact, the person is taking the drug. In addition to taking the chemicals the patient's body may not be absorbing or reacting as intended to the chemical. Knowledge of the treatment plan and the testing results enable the plan to be modified so that it has its best chance of working and also least chance of doing harm.

A treatment plan must be followed to work. A treatment plan must be managed and adjusted based on testing. Non-adherence is a major problem that limits the effectiveness of many treatment plans. And also causes problems where medical and nutritional professional may make dangerous or erroneous suggestions based on the false data non-adherence generates. For example, a doctor may increase a person's medications based on the assurances that the patient is taking a medication when in fact they are not taking the medication. This can be dangerous for the user and for the public.

Patients often want to comply with treatment regimens but there are many reason why they are unable and shift into non-adherence. Willpower exhaustion, a lack of planning, disorganization, misunderstanding the dosing instructions, forgetfulness, running out of the drug, and other reasons make coordination and administration of the regimen to be burdensome. It is often especially difficult for people with mental illness diseases to track, plan, dose, and continue to adhere to the treatment plan. For example, people with bipolar, schizophrenia, or schizoaffective disorders may find it especially difficult to remain compliant to a designed regimen when they are feeling okay or feeling normal. It is essential for many people, often life and death, to adhere to their treatment regimes.

Too many people fail at treatment adherence because it is a task that takes time, energy, organization, and must be done consistently. It is a massive effort that is difficult for healthy people to follow and even more difficult for ill people to follow. The failure to comply with a drug regimen results in increased costs from the providers and expenses from the user.

SUMMARY OF TIIE DISCLOSURE

What is needed is a substance delivery device having vaporization or atomization capabilities paired with at least one substance cartridge comprising a beneficial substance and an addictive substance. A user places a mouthpiece of the device in his/her mouth to draw air through an air intake comprising a predetermined concentration of a beneficial substance and an addictive substance, or an addictive substance and a placebo, or a beneficial substance and a placebo.

The device comprises external control, connectivity, and notification features to promote compliance and to collect, process, and send regimen compliance information to a health care provider or prescriber.

The predetermined concentrations and dosages for each substance or placebo is regulated by the device's computer system. A prescriber or treatment provider programmatically configures the dose, concentration, and frequency. The instructions are stored in a data storage and processed by a controller and memory.

A beneficial substance is prescribed and filled or otherwise obtained in a cartridge. The cartridge comprises at least two bladders or a bifurcated chamber to contain the beneficial substance and the addictive substance. However, in other embodiments, the beneficial substance and the addictive substance may be mixed and contained in one cartridge bladder. In some embodiments, a cartridge comprises an addictive substance, a beneficial substance, and a placebo.

BRIEF DESCRIPTION OF THE DRAWINGS

The accompanying drawings that are incorporated in and constitute a part of this specification illustrate several embodiments of the disclosure and serve to explain the principles of the disclosure.

NUMERALS OF THE FIGURES

Figure 1:
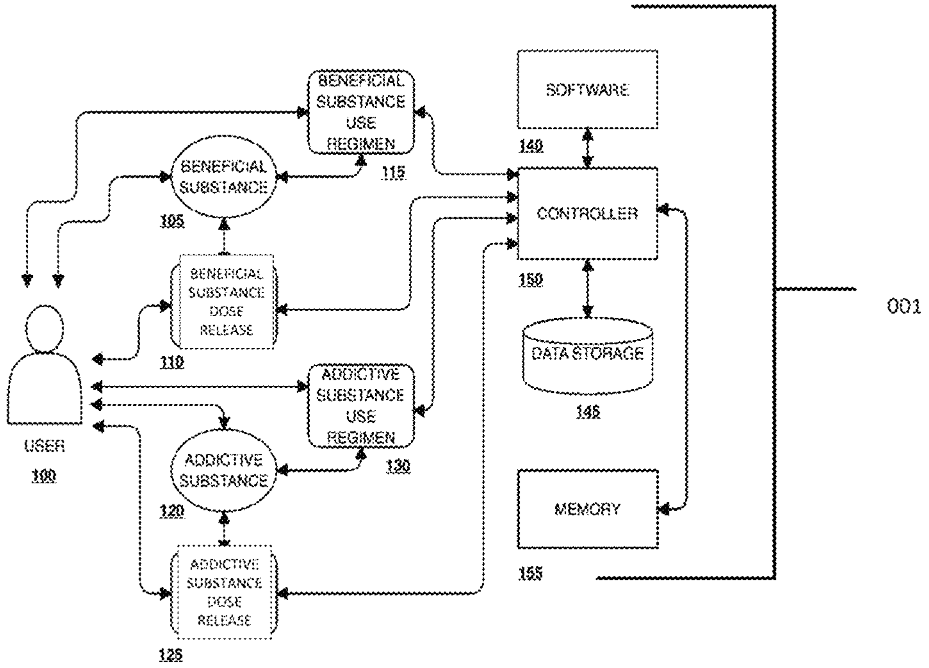
FIG. 1 illustrates an exemplary schematic of a system is shown.

001 atomizer/vaporizer device ("device") computer
100 user
105 beneficial substance
110 beneficial substance dose release
115 beneficial substance use regimen
120 addictive substance
125 addictive substance dose release
130 addictive substance use regimen
140 software
150 controller
145 data storage
155 memory
200 atomizer/vaporizer device ("device")
203 device housing
205 control scroll PREVIOUS button
206 control scroll NEXT button
207 control SELECT button
208 display
210 speaker
215 cartridge connector
220 substance in-port
225 light-emitting diode
230 data port
235 optical encoder
240 drive shaft
245 battery
250 mouthpiece out-port
255 cartridge location 1
256 cartridge location 2
257 cartridge location 3 (Not Shown)
258 cartridge location 4 (Not Shown)
260 Bluetooth notification
265 WiFi notification
270 power button
300 cartridge
305 substance bladder
310 substance fill port
315 substance feed line
320 rotor
325 roller
330 shaft hole
335 snap connector
340 cartridge out port
345 rotor alignment spindle
350 cartridge data chip
360 light-emitting diode lens
400 heating element
410 heating chamber
415 substance check valve CLOSED
416 substance check valve OPEN
420 air intake aperture
425 air check valve
430 pressure sensor
440 inhale check valve
450 mouthpiece
455 vapor out-port
500 user
510 substance prescriber
515 substance prescriber prescribes beneficial regimen for user
520 beneficial substance regimen is created
530 pharmacist/dispensary
525 pharmacist; dispensary fill prescription making the cartridge
536 filling cartridge with beneficial substance
537 endowing of beneficial regimen into cartridges data chip
538 optionally printing label containing beneficial regiment data for user or attaching to cartridge
540 user takes custody of cartridge
550 user attaches cartridge to device
555 device validates cartridge using data in the device, in the cartridge data chip and optionally from the cloud or an app
560 determining whether cartridge valid determination is made
565 determining that if the cartridge is not valid then an error condition is created and relevant parties are notified
570 determining if the cartridge is valid then the user is told they are able to use the device and cartridge

DETAILED DESCRIPTION

In some embodiments, addictive substance to create an addiction schedule that is aligned with a subject's desired healthful regimen. Using the compelling power of an addiction to create the act of dosing with a device and then also delivering a beneficial substance at set times or based on other pre-determined parameters can greatly help a user adhere to his/her treatment.

The disclosure relates to using a controlled addiction to bias a person to comply with necessary drug regimens. Patients who rely on drugs to maintain their health but are unable to or find it difficult to maintain proper medical drug use schedules could be helped by a strong and controlled addiction that aligns with their drug use schedule and a drug metering system that dispenses medical drugs along with the controlled addictive substance.

For example, nicotine is a highly addictive substance with mild side effects. Exemplary devices utilize a pre-programed metering system to dispense a prescribed dose of at least one beneficial substance as well as a controlled addictive substance to bias the person to use the system and thus achieve treatment adherence.

In one regimen example, a user is prescribed critical medication to promote mental stability or to improve chemical imbalances in the central nervous system. An exemplary device that has two or more tanks, one including the critical medication or beneficial substance and the other including synthetic or naturally-derived nicotine, pre-determined treatment regimen software instructions that are processed and control the dosage and concentration from the bipolar med tan. The device monitors via sensors and collects information in a tracking system that ensures the user is getting the correct dose of the beneficial substance. In addition, a device may contain a sensing system to check the user's vitals and may contain an notification or alert system.

The user will begin using the device and will get notices (via sounds, light, text, or etc) and will be dosed with nicotine and/or the beneficial substance depending on the dosage needs of the user and the need to maintain the addiction for the user's benefit. As the user uses the device, it will track their use and either dose nicotine and the beneficial substance, nicotine only, or beneficial substance, and as necessary. In some embodiments, a placebo may be added and dispensed as well, especially for weaning and reducing tolerance build ups.

As the user uses the device, a profile is generated of the user and a dosing schedule is formed that determines correct doses of nicotine and beneficial substance to bias the user to their scheduled medical regimen. All information is tracked in the device and can be reviewed and updated by a medical professional.

The device can also notify others if the person is out of compliance. The device can also gamify the use of the device to make it fun to use. Sensors in the mouthpiece and/or grip can test the person's state (i.e. breath and saliva and temperature and heart rate and etc.) and track that information and then adjust doses based on the information.

Additional tanks can be added to enable a person to be given multiple doses of different drugs so their entire drug/beneficial substance regimen, including medical and supplemental (vitamin D, cod liver oil, etc.) could be included in the program. The system would have beneficial substances in tanks that included dosing information, batch numbers, serial numbers and other related information in a form readable by the device dispensing the substances via atomization or via vaporization.

Addictive substances may be nicotine, caffeine, sugar, or any other suitable excipient. Beneficial substances may be any liquid suspension or mixture suitable for oral or nasal administration.

Referring to FIG. 1, an exemplary system schematic is shown. User 100 will take Beneficial Substance 105 in accordance with Beneficial Substance Use Regimen 115 via Beneficial Substance Dosing Means 110. To assist User 100 in maintaining compliance with Beneficial Substance Use Regimen 115 this system uses an Addictive Substance 120 according to an Addictive Substance Use Regimen 130 that is administered via an Addictive Substance Dosing Means 125.

Controller 150 reads Beneficial Substance Use Regimen 115 and Addictive Substance Use Regimen 130 to determine how to best meet the User 100 needs. As User 100 uses the device Controller 150 will determine if it is appropriate to dose User 100 with the Beneficial Substance 105, based on the Beneficial Substance Use Regimen 115. And if it is Controller will dose User 100 using the Beneficial Substance Dosing Means. Software 140 running on Controller 150 will review Beneficial Substance Use Regimen 115 against User 100 actual use data which can be stored in Memory 155 and/or Data Storage 145 and will determine if User 100 is in compliance with Beneficial Substance Use Regimen 115, or not in compliance with Beneficial Substance Use Regimen 115. A user can be under or over compliant with the Beneficial Substance Use Regimen 115. Under-compliant means the user is taking less than the required doses of Beneficial Substance 105 based on the Beneficial Substance Use Regiment. While over-compliant means the user is taking too much of the Beneficial Substance 105 based on the Beneficial Substance Use Regimen 115. If User 100 is under-compliant then Controller will dose Addictive Substance 120 along with the Beneficial Substance 105. The effect is User 100 desire to use the device will increase.

If User 100 is over-compliant then Controller will dose Beneficial Substance 105 without Addictive Substance 120.

Figure 2:
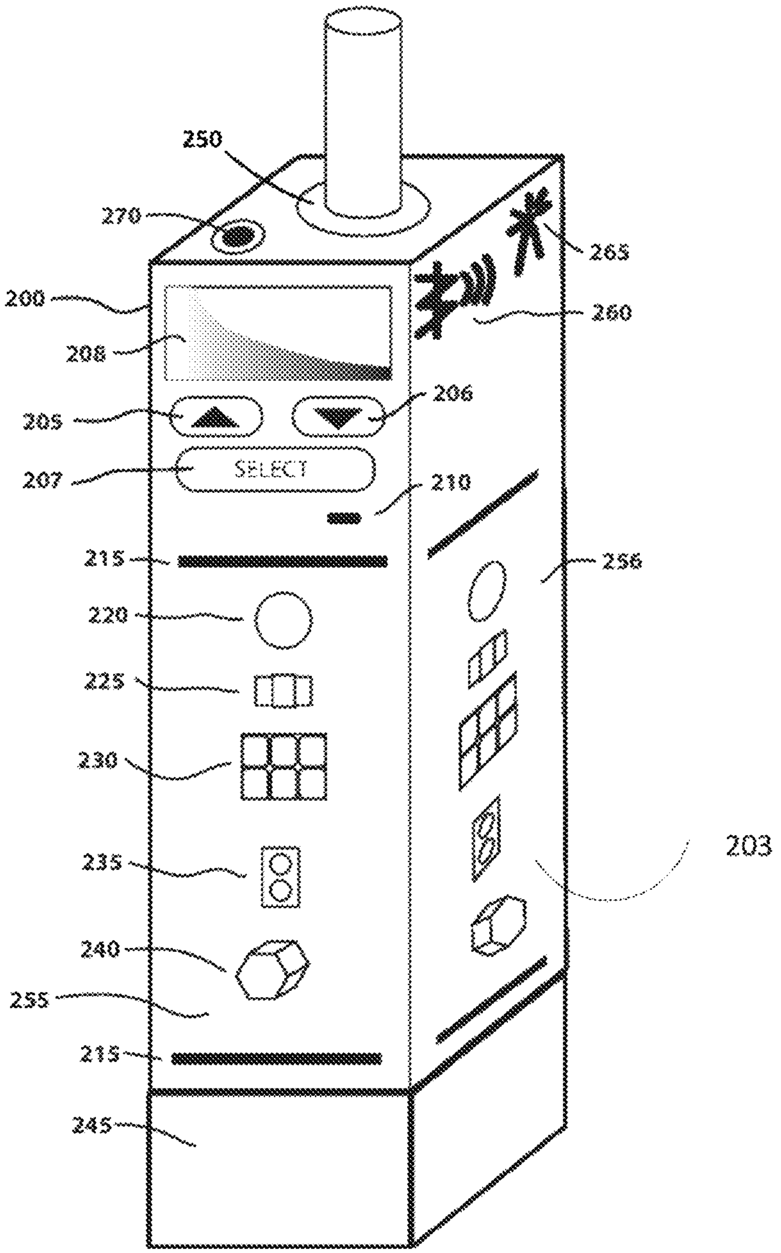
FIG. 2 illustrates a perspective view of an exemplary device with external components.

Referring to FIG. 2, an exemplary device is shown in a perspective view of the device housing and external components. Atomizer/Vaporizer Device has Controls including buttons to Select, Scroll Next, Scroll Previous, and a Display to see menus, menu options, and device parameters. Atomizer/Vaporizer Device has a Speaker to alert and notify the User. A cartridge (not shown) attaches to Atomizer'Vaporizer Device by connecting to the connector which aligns Substance IN-PORT, LED, Data Port, Optical Encoder, and Drive Shaft. A connected Battery provides power.

When User presses the Power Button the device powers up. A controller (not shown) checks for cartridges by reading the data port. If a cartridge (not shown) is attached the data port will read the cartridges associated data and determine if there is enough valid information to enable the cartridge to be used by the User. If the cartridge is valid the Atomizer/Vaporizer Device will notify the user which can be via a sound from the speaker, a visual indication from the LED, a message on the display, or a combination thereof.

A pressure sensor (not shown) in the device checks for User applied pressure at the mouthpiece OUT-PORT. And if pressure is sensed the device will determine the amount of cartridge substance (not shown) to dispense into the IN-PORT for atomization/vaporization and inhalation by the User via OUT-PORT.

The atomization/vaporization device calculates the correct amount of cartridge substance (not shown) using data from the cartridge's associated data which is read by the data port. Accurate calculations of dispensed substances can be made knowing the diameter of the cartridge feed tube and by reading the cartridge's flow data in coordination with the optical encoder that tells how far the drive shaft moved the cartridge's feed wheel (not shown).

The atomizer/vaporizer device captures use and other data that is stored and can be transmitted to other devices. Transfer means may include wired or wireless connections including, but not limited to, Bluetooth, WiFi, infrared, USB, or other common means of transmitting data.

The atomizer/vaporizer device is run by a controller (not shown) and can be run with 1 to many cartridges in multiple combinations containing different substances. The atomizer/vaporizer device dispenses cartridge substances according to the parameters included in the cartridge's data chip and can run checks to ensure the combination of cartridges and their associated substances pass a DUR (Drug Usability Review). This can be performed in real-time locally at the device or via the device interacting with a computer severe over the Internet and the device's Wifi connection. It can also be connected to an app and parameters that control the device's operation can be modified, updated, changed, or confirmed.

Figure 3:
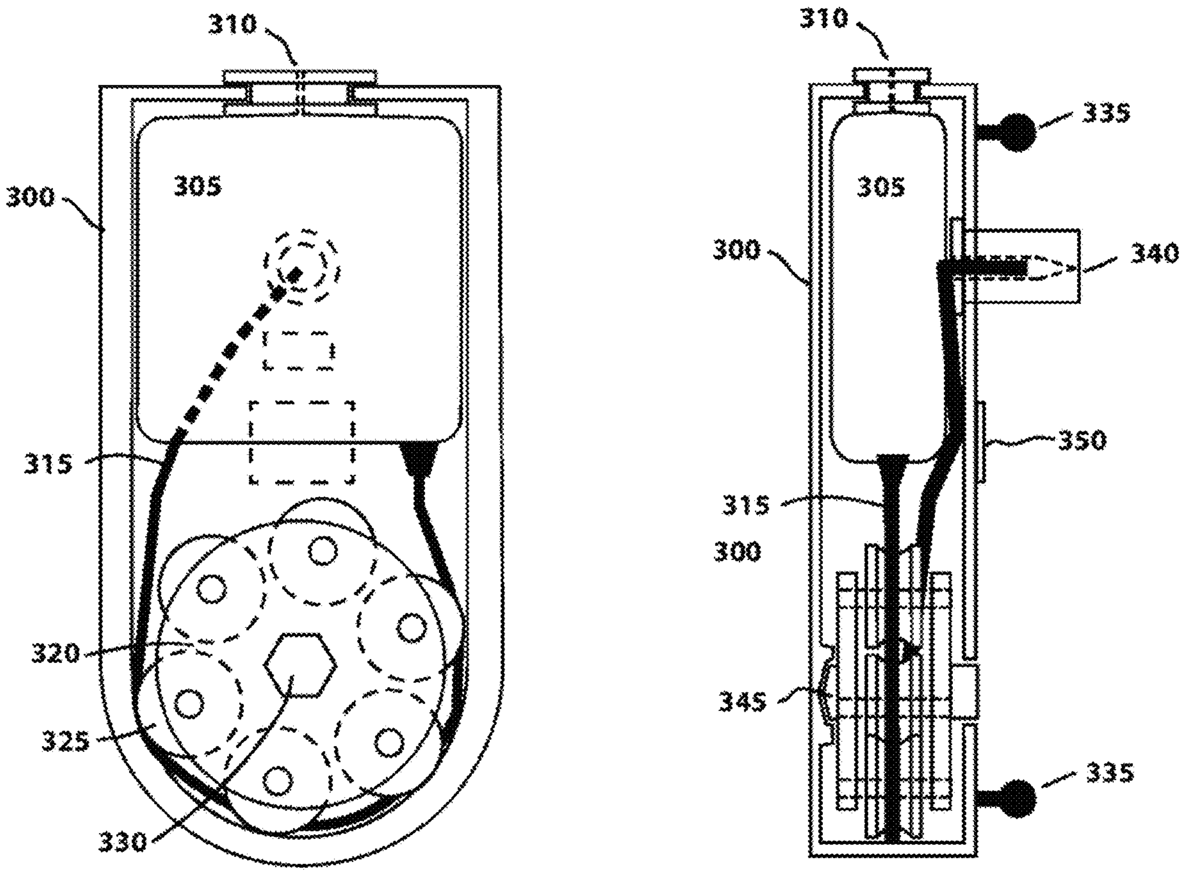
FIG. 3 illustrates an internal front and side view of an exemplary cartridge.

Referring to FIG. 3, an interior front and side view is shown of an exemplary cartridge. Cartridge contains a Substance Bladder with a fillable IN-PORT and a Rotor with attached Rollers (or alternatively shoes) that interfaces with a Substance Feed Line for the purposes of the on command delivery of the Substance to the aerosolization mechanism inside the atomizer/vaporizer device (show in FIG. 2). The cartridge is attached to the atomizer/vaporizer device by snap connects that enable it to be attached and detached as needed. The snap connectors also align and supply the pressure needed for the data port to read and write to the cartridge data chip.

When attached a cartridge to the atomization/vaporization device a controller (not shown) reads the cartridge data chip and determines how, when, and if it can use the cartridge. The controller notifies the user if there is a problem with the cartridge or the substance, eg cartridge is expired, the cartridge is empty, the substance in the cartridge is not compliant with the other cartridges, the substance is unable to be properly dosed in the current device, and other such reasons for the cartridge to be unauthorized for use. Otherwise, the atomizervaporizer will notify the user that the cartridge is authorized for use.

When the atomization/vaporization device determines the cartridge is authorized for use it may use the cartridge in the following manner. When the atomization/vaporization device sense the pressure of a user inhaling from the atomization/vaporization device's OUT-PORT the controller will drive the Roller the rotations required to dispense the correct dose using the optical markings on the Rotor and the optical encoder in the atomizer/vaporizer device. The dose of the substance will be ejected out of the Cartridge OUT-PORT. Correct dosing is determined by data in the Cartridge Data Chip that is attached to the cartridge and updated when the bladder is filled.

The LED Lens is used to indicate different modes of operation and can also be used for decoration. For example, if there is a cartridge error it will be beneficial to the user to know which cartridge the error relates to. Flashing the cartridge associated with the error the color red will instantly help the user find the right cartridge. Lighting a cartridge green could tell the cartridge is ready for use. And other colors can also be tied to meaningful designations like yellow meaning “almost out, time to reorder”, blue meaning “take with water”, and other conditions that can be programmed into the atomization/vaporization device and/or the cartridge data chip and then used by the atomization/vaporization device to communicate valuable information about the cartridge to the user.

Figure 4:
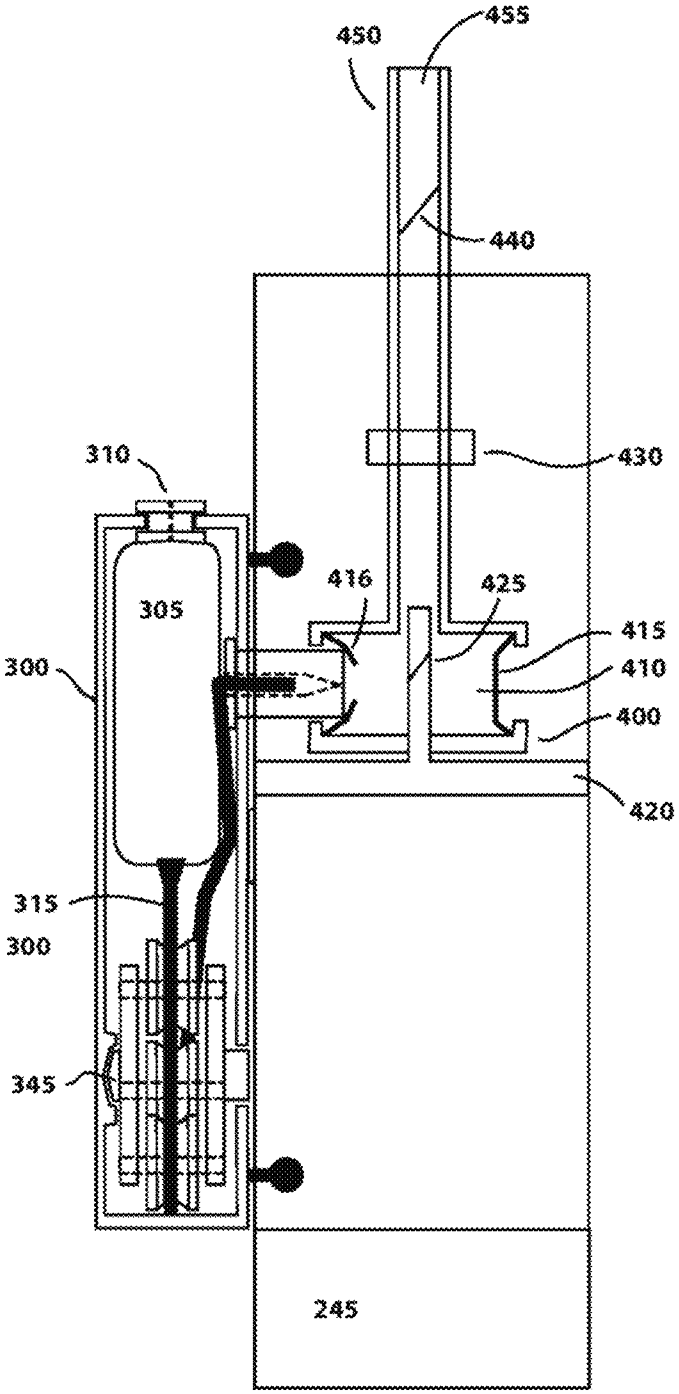
FIG. 4 illustrates a front interior view of an exemplary device with a cartridge.

Referring to FIG. 4, a front interior view of an exemplary device with a cartridge attached is shown. When the User and device are ready to use the user inhales on the Mouthpiece which is sensed by the pressure sensor. The controller heats up Heating Element and Dispenses Substance from the Cartridge, shown on one side, into the Heating Chamber. The Heating Element vaporizes the substance and mixes it with air from the Air Intake Aperture. The vapor opens the check valves and is inhaled by the user.

Figure 5:
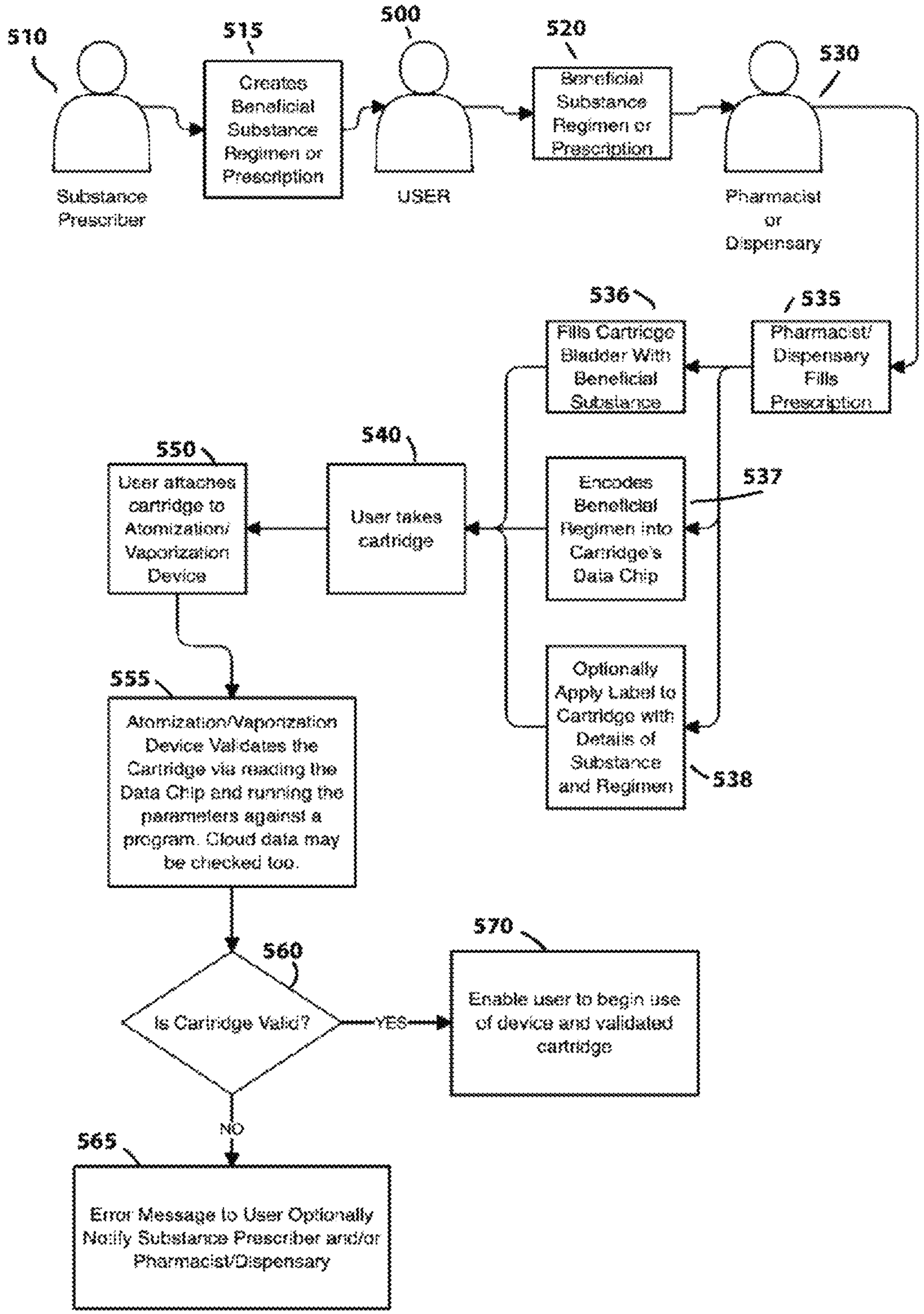
FIG. 5 illustrates an exemplary system flow chart.

Referring to FIG. 5, an exemplary system flow chart is shown. The exemplary steps are as represented in FIG. 5.

A number of embodiments of the present disclosure have been described. While this specification contains many specific implementation details, these should not be construed as limitations on the scope of any disclosures or of what may be claimed but rather as descriptions of features specific to particular embodiments of the present disclosure.

Certain features that are described in this specification in the context of separate embodiments can also be implemented in combination in a single embodiment. Conversely, various features that are described in the context of a single embodiment can also be implemented in combination in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while methods and steps are depicted in the drawings in a particular order, this should not be understood as requiring that such operations be performed in the particular order shown or in sequential order, or that all illustrated operations be performed, to achieve desirable results.

Thus, particular embodiments of the subject matter have been described. Other embodiments are within the scope of the following claims. In some cases, the actions recited in the claims can be performed in a different order and still achieve desirable results. Nevertheless, it will be understood that various modifications may be made without departing from the spirit and scope of the claimed disclosure.

What is claimed is:

1. A device, comprising: a device housing having external components comprising control buttons, light-emitting diodes, and notification indicators;

a mouthpiece out port accommodating a mouthpiece, wherein the mouthpiece has a vapor out-port, and the mouthpiece extends externally from the device housing, through the mouthpiece out port, and vertically into the housing to a pressure sensor;

a heating chamber with heating element that is vertically connected to an air intake aperture that extends through the heating chamber to the mouthpiece vapor out-port;

a cartridge having a cartridge out port that connects laterally to a substance in-port of the device housing and into the heating chamber, wherein the cartridge houses a substance bladder having a substance fill port, wherein the bladder is connected to a substance feed line that wraps around a rotor and through an open substance check valves;

a battery; and a cartridge connector apparatus on the device housing that is coordinated to removably receive a snap connecter apparatus of the cartridge;

wherein the device delivers a beneficial substance and an addictive substance contained in the substance bladder to a user; and wherein the inclusion of the addictive substance improves the user's compliance with a beneficial substance regimen.

2. The device of claim 1, wherein the cartridge further comprises a cartridge data chip that contains treatment regimen software containing instructions for substance dosage and concentration of the beneficial substance and for the addictive substance in accordance with the beneficial substance use regimen and an addictive substance use regimen administered concurrently.

3. The device of claim 1, wherein the addictive substance is nicotine, caffeine, or sugar.

4. The device of claim 1, wherein the mouthpiece further comprises an inhale check valve.

5. The device of claim 1, wherein the air intake aperture further comprises an air check valve.

* * * * *